United States Patent [19]

Przybylowicz et al.

[11] Patent Number: 4,943,415

[45] Date of Patent: Jul. 24, 1990

[54] GROOVED COVER FOR TEST ELEMENTS

[75] Inventors: Catherine S. Przybylowicz, Rochester; Merrit N. Jacobs, Fairport; Joseph S. Douglas, Rochester, all of N.Y.

[73] Assignee: Eastman Kodak Company, Rochester, N.Y.

[21] Appl. No.: 380,839

[22] Filed: Jul. 14, 1989

[51] Int. Cl.$^5$ .................... G01N 35/00; G01N 35/02
[52] U.S. Cl. ..................................... 422/56; 422/58; 422/63; 422/64; 422/65; 422/82.05
[58] Field of Search .................... 422/56, 58, 63, 64, 422/65, 67, 68

[56] References Cited

U.S. PATENT DOCUMENTS

| 4,298,571 | 11/1981 | DiFulvio et al. | 422/65 |
| 4,568,519 | 2/1986 | Hamilton et al. | 422/63 |
| 4,584,275 | 4/1986 | Okano et al. | 436/46 |
| 4,798,705 | 1/1989 | Jakubowicz et al. | 422/63 |
| 4,814,279 | 3/1989 | Sugaya | 422/63 |

Primary Examiner—Robert J. Warden
Assistant Examiner—Kimberly A. Trautman
Attorney, Agent, or Firm—Dana M. Schmidt

[57] ABSTRACT

There is described a cover for test elements for use in stations of an analyzer that are downstream from the sample-spotting station. The cover is improved in that its undersurface is grooved lengthwise to accommodate a drop of sample protruding from the test element. However, the clearance groove does not extend the full length of the cover, to prevent significant evaporation.

4 Claims, 2 Drawing Sheets

GROOVED COVER FOR TEST ELEMENTS

FIELD OF THE INVENTION

The invention concerns evaporation covers used in analyzers, especially such a cover for test elements that have sample drops protruding therefrom.

BACKGROUND OF THE INVENTION

Clinical analyzers have for years provided rapid and accurate tests using slide-like test elements, as described, for example, in U.S. Pat. No. 4,298,571. Incubators have been used in such analyzers, along with preheat stations, to control the temperature of the test element while a patient sample drop spotted thereon undergoes a chemical reaction to produce a detectable change. That is, a test element is transferred from a spotting station to a preheat station, to an incubator, and then to a change-detecting station.

In most of the stations following the spotting station, a cover is used to contact the spotted test element to prevent significant evaporation of the sample. Such a cover is illustrated in FIG. 4 of the aforesaid '571 patent. Because some of the test elements are potentiometric types that have sample and/or reference drops protruding from the test element for a long time, as shown in said FIG. 4, the cover is grooved from side to side to allow clearance of such a drop. There is no need and no provision, however, in such covers, for the grooves to run from the exterior edge at which the test element enters, lengthwise along the direction of movement of the test element, since a piston is used to raise and lower the cover. Instead, the groove runs perpendicular to the direction of slide movement. Furthermore, the groove does not extend to any edge surface of the cover.

Such covers with such undercut grooves have been used for potentiometric test elements, because the drops on such elements have protruded above the rest of the test element. Such protrusion after spotting has not been a significant problem with most colorimetric elements, at least, not the type also useful with the analyzer of the '571 patent, since sample absorption is much more rapid in such colorimetric elements.

A problem has arisen, however, in the design of new analyzers that are to operate at higher throughput speeds to provide increased efficiency. Such new analyzers require a preheat station that receives colorimetric or rate test elements so soon after spotting, e.g., 500 millisec afterwards, that the drop still protrudes above the test element. Conventional covers in stations following the spotting station, e.g., the preheat station, have been unsatisfactory since they are designed to fit with an undersurface that is in flush contact with the test element. Such flush fit means the drop is wiped onto the undersurface as the test element is advanced into the particular station. This in turn produces unacceptable contamination of the cover and loss of sample volume. The first attempt at solving the problem was to provide a longitudinal groove extending the full length of the cover. This, however, was a failure due to the rapid evaporation that such a groove allowed to the drop.

Therefore, there has been a need prior to this invention to meet three competing goals: to provide a cover undersurface constructed in a way that does not wipe the drop of a colorimetric element, to keep such a drop from experiencing significant evaporation, and to minimize gaseous carryover.

RELATED APPLICATIONS

Commonly-owned U.S. application Ser. No. 346,205 filed on May 2, 1989 by Shaw et al., entitled "Universal Evaporation Cover" described an incubator cover having an undersurface that is raised away by its front corners from a test element as the latter is moved into the incubator. However, once a colorimetric test element is in place, that undersurface completely contacts the test element and no groove exists to clear a drop that may protrude. In fact, the clearance that exists while the test element is still moving in is not a closed groove, but one that is open all the way to the end, FIG. 2.

SUMMARY OF THE INVENTION

We have designed a cover that overcomes these problems.

More specifically, there is provided a clinical analyzer for use with slide-like test elements spotted with a drop of patient sample, the analyzer including stations that follow a spotting station that places the drop onto each test element, at least some of the following stations including a cover having a surface in contact with each test element after it is spotted, and means for moving a test element a predetermined direction into each of the following stations from an exterior location to an interior location under the cover, the moving being done while the moved test element is in contact with the cover. The analyzer is improved in that at least one of the cover contact surfaces has a closed groove extending from the cover edge adjacent to the exterior location, to the interior location, the groove (a) being closed at its end corresponding to the interior location, (b) having an orientation axis that parallels the predetermined movement direction, and (c) having a clearance and shape adequate to accommodate without contact any sample drop of a predetermined volume protruding from the test element.

Accordingly, it is an advantageous feature of the invention that a cover is provided for already-spotted colorimetric or rate test elements that avoids contacting drops of sample not yet absorbed, without significant evaporation occurring.

Another advantageous feature is that such a cover can be constructed of a variety of materials and still prevent undesired carry-over of gaseous byproducts to subsequent test elements.

Other advantageous features will become apparent upon reference to the following description of the preferred embodiments when read in light of the attached drawings.

BRIEF DESCRIPTION OF THE DRAWINGS

FIG. 5 is a section view taken generally along the line V—V of FIG. 4.

DESCRIPTION OF THE PREFERRED EMBODIMENTS

The invention is particularly described regarding its use in a preheat station between the spotting station and the incubator, to process colorimetric-type test elements. In addition, it is useful with other types of test elements and in other stations that follow the spotting station, including the incubator, provided that the residence time of the test element in such other stations, and the flow rate of air in the vicinity of the cover, are such as to restrict significant evaporation. As used herein, evaporation is "significant" if the loss of fluid exceeds 0.5 µl.

Figure 1:
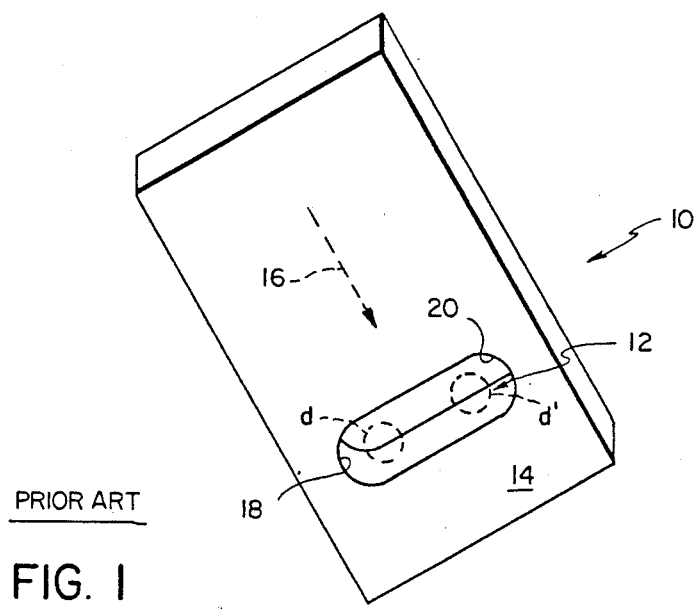
FIG. 1 is a perspective view of the undersurface of a cover of the prior art.

In the prior art, FIG. 1, a cover 10 such as is shown in the aforesaid U.S. Pat. No. 4,298,571, has a groove 12 in undersurface 14 that extended transversely to the direction of movement, arrow 16, of a test element under the cover. Groove 12 did not extend the full width, but was closed at both ends 18, 20. Its depth was such as to accommodate (without touching) two drops, shown in phantom as d and $d_1$, of a potentiometric test element E', also in phantom.

Figure 2:
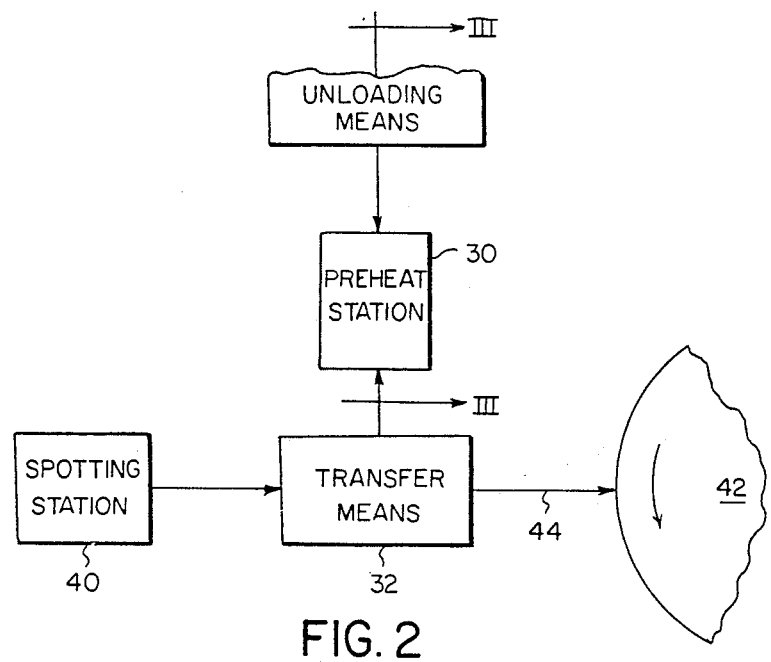
FIG. 2 is a fragmentary schematic view of an analyzer constructed in accord with the invention.

In the invention, the improved cover is preferably used in a preheat station 30, FIG. 2, that receives test elements from transfer means 32, which in turn receives each test element from a spotting station 40 and sends preheated elements on to an incubator 42, which can be any conventional incubator such as the rotating one shown. Transfer means 32 preferably comprises, FIG. 3, a support platform 34 and a pusher blade 36, to push a spotted test element E into station 30 (also shown in phantom, FIG. 4). A conventional pusher blade 38 can be used to return preheated elements to transfer means 32, where another mechanism, not shown, is effective to forward a test element as shown by arrow 44, FIG. 2. Alternatively, a more complicated finger arrangement (not shown) can be used to replace blades 36 and 38, FIG. 3, in that the fingers both feed elements into preheat station 30, and return elements from that preheat station.

Preheat station 30 preferably comprises an element support surface 50, a cover 52, and biasing means 54 for biasing the cover down onto a test element E. Any biasing means will suffice, such as conventional compression springs. Cover 52 includes a boss 56 to cooperate with the biasing means, and a camming lip 58 to encourage a test element to be inserted between the cover and support surface 50.

Figure 4:
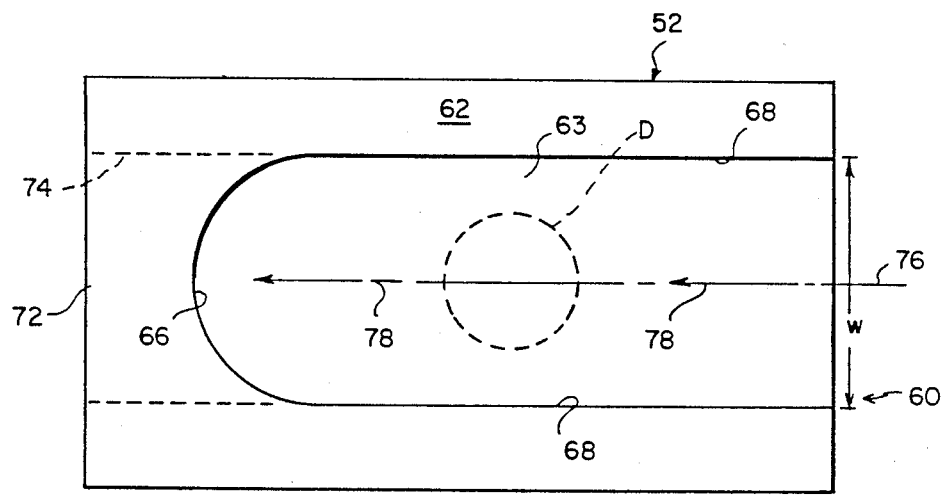
FIG. 4 is a bottom plan view of the cover shown in FIG. 3.
Figure 3:
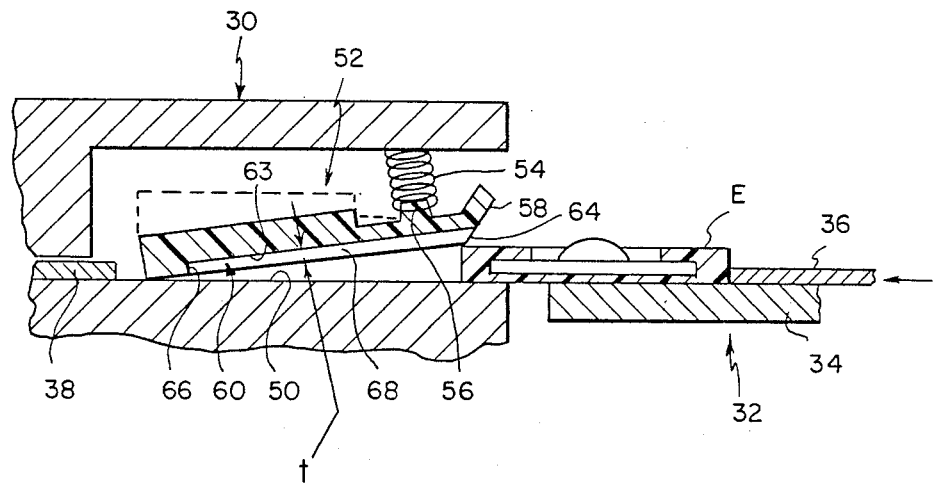
FIG. 3 is a fragmentary section view taken generally along line III—III of FIG. 2.

In accordance with one aspect of the invention, cover 52 comprises, FIGS. 3 and 4, a groove 60 in undersurface 62 extending lengthwise from lower edge 64 of lip 58. That is, edge 64 is the leading edge of undersurface 62, FIG. 4, that is adjacent the exterior of the station 30, FIG. 3, from whence comes a test element for insertion. However, groove 60 having bottom surface 63 is closed at end wall 66 that is interior of the station, leaving sidewalls 68 extending from end wall 66 to edge 64. The purpose of closed end 66 is to keep circulating air from readily reaching a drop surrounded by sidewalls 18 and end wall 66, FIG. 4, the position of a drop D being shown in phantom. The width "w" of the groove, FIG. 4, as well as its depth "t", FIG. 3, are selected to keep the drop from contacting any of the cover, for drop volumes no greater than 20 µL, and preferably volumes of 10 µL. Recognizing that some static electricity can attract the drop, "t" is most preferably at least about 0.254 mm. The reason is that the clearance between bottom surface 63 of the groove and the top of a protruding drop, is preferably at least 0.18 mm, the drops having a volume no greater than about 12 µl and thus a protrusion above the plane of the test element's exterior surface that is preferably about 0.17 mm.

End wall 66 can be made quite thin, that is, can closely approach opposite edge 72 of cover 52. However, if groove 60 were to extend the full length as suggested by phantom lines 74, it would provide too much evaporation of drop D, and be inoperative.

Groove 60 has its long axis 76 oriented so as to be parallel to the direction of movement of the test element, such direction being shown as arrows 78, FIG. 4.

Thus, as is shown in FIG. 5, the cover 52 sits on top of element E with groove 60 providing adequate clearance for a protruding drop D on the element.

Any material is useful for surfaces 62 and 63. Preferably, however, it is Teflon or polyethylene. Surprisingly, Teflon is equally as good in this configuration in preventing carryover of $SO_2$ gas generated by phosphorus-testing test elements, compared to polyethylene. This result was found not to exist heretofore, and is in contrast to that previously reported in commonly owned and previously invented U.S. application Ser. No. 346,206 filed on May 2, 1989 by Jacobs et al, entitled "Polyethylene Evaporation Covers".

The invention has been described in detail with particular reference to preferred embodiments thereof, but it will be understood that variations and modifications can be effected within the spirit and scope of the invention.

What is claimed is:

1. In a clinical analyzer for use with slide-like test elements spotted with a drop of patient sample, said analyzer including stations that follow a spotting station that places said drop onto each test element, at least some of said following stations including a cover having a surface in contact with each test element after it is spotted, and means for moving a test element a predetermined direction into each of said some stations from an exterior location to an interior location under said cover, said moving being done while the moved test element is in contact with said cover;

the improvement wherein at least one of said cover contact surfaces has a recessed groove extending from the cover edge adjacent to said exterior location, to said interior location, said groove (a) being closed at its end corresponding to said interior location, (b) having an orientation axis that parallels said predetermined movement direction, and (c) having a clearance and shape adequate to accommodate without contact any sample drop of a predetermined volume protruding from said test element, said groove being smaller in width than the width of a slide-like test element covered by said cover.

2. An analyzer as defined in claim 1, wherein at least one of said stations having said at least on cover surface is a preheat station prior to an incubator.

3. An analyzer as defined in claim 1 or 2, wherein said clearance is at least about 0.18 mm above the height a 10 µl drop of liquid can occupy on a test element before it is absorbed therein.

4. An analyzer as defined in claim 1 or 2, wherein said at least one surface comprises a material selected from Teflon or polyethylene.

* * * * *